United States Patent [19]

Peterson

[11] Patent Number: 5,534,010

[45] Date of Patent: *Jul. 9, 1996

[54] CLOSURE FOR A SKIN WOUND OR INCISION

[76] Inventor: Meldon L. Peterson, 912 SW. 11th St. #1, Newport, Oreg. 97365

[ * ] Notice: The term of this patent shall not extend beyond the expiration date of Pat. No. 5,176,7030.

[21] Appl. No.: 302,711

[22] PCT Filed: Oct. 29, 1992

[86] PCT No.: PCT/US92/09246

§ 371 Date: Apr. 29, 1994

§ 102(e) Date: Apr. 29, 1994

[87] PCT Pub. No.: WO93/08748

PCT Pub. Date: May 13, 1993

[51] Int. Cl.⁶ .................................................. A61B 17/04
[52] U.S. Cl. ................................. 606/215; 606/216
[58] Field of Search ...................... 606/213–216

[56] References Cited

U.S. PATENT DOCUMENTS

| | | | |
|---|---|---|---|
| 2,196,296 | 4/1940 | Flynn | 606/215 |
| 2,752,921 | 7/1956 | Fink | 606/215 |
| 4,423,731 | 1/1994 | Roomi | 606/215 |

FOREIGN PATENT DOCUMENTS

| | | |
|---|---|---|
| 0551713 | 6/1932 | Germany . |
| 0578512 | 6/1933 | Germany . |
| 1903085 | 9/1969 | Germany . |

*Primary Examiner*—Gary Jackson
*Attorney, Agent, or Firm*—Marger, Johnson, McCollom & Stolowitz

[57] ABSTRACT

A sutureless closure for a skin wound or incision, which includes first and second strips of adhesive tape adapted to adhere to skin adjacent either side of the wound. A third strip of adhesive tape is provided to adhere to the upper exposed surface of the first strip of tape. A plurality of filaments are secured between the ends of the first and third strips of tape, with the filaments being slidably received over structure defined on the second strip. Also provided are means for frictionally engaging the skin closely adjacent the opposing ends of the first and second tapes so that tension in the filament draws tissue the engaging means into a slight mound. A protective strip covers the adhesive on the first and third strips with the protective strip including a pair of transfer creases to permit each of the adhesive strips of tape which the protective strip covers to be covered by the same side of the strip.

10 Claims, 4 Drawing Sheets

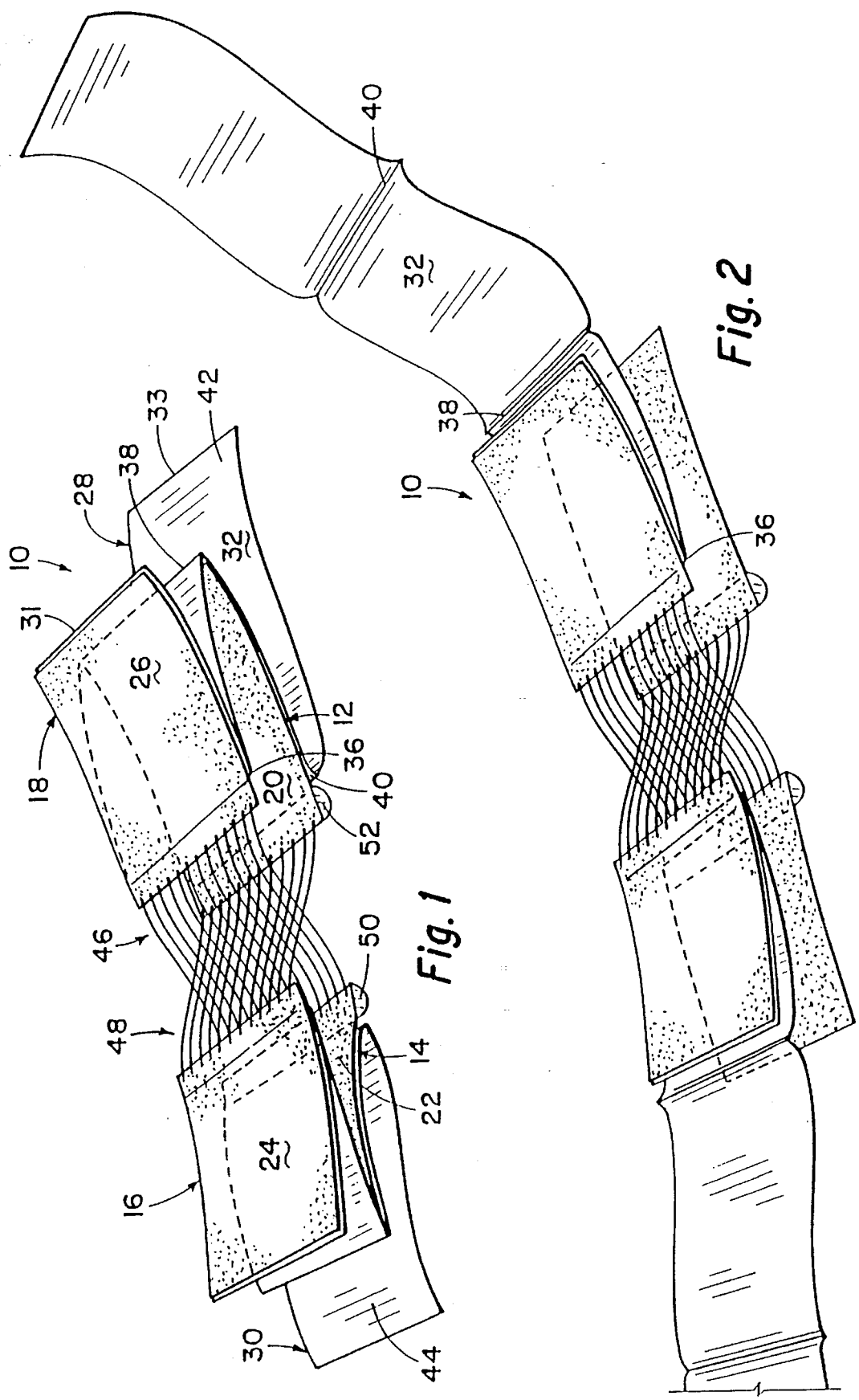

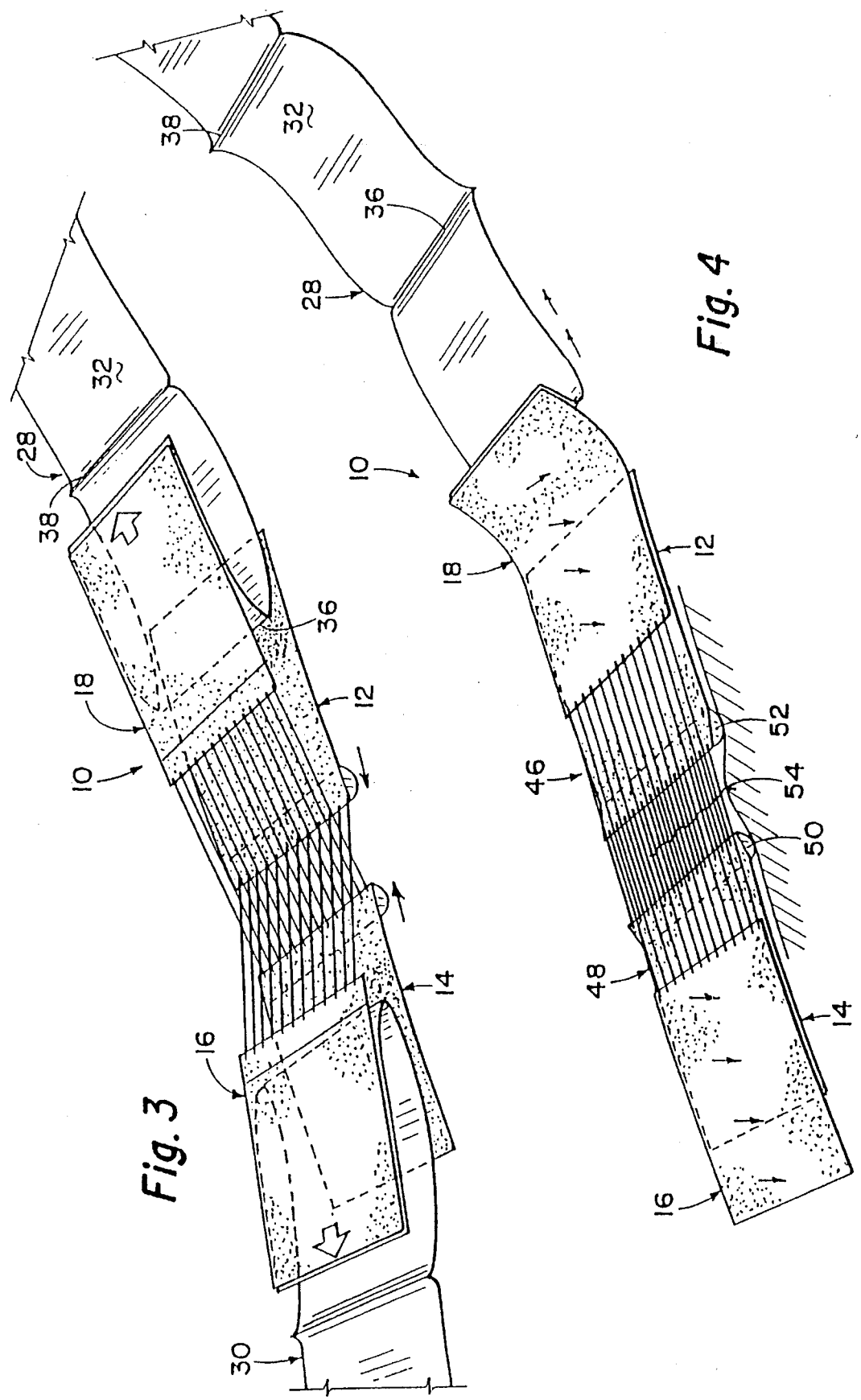

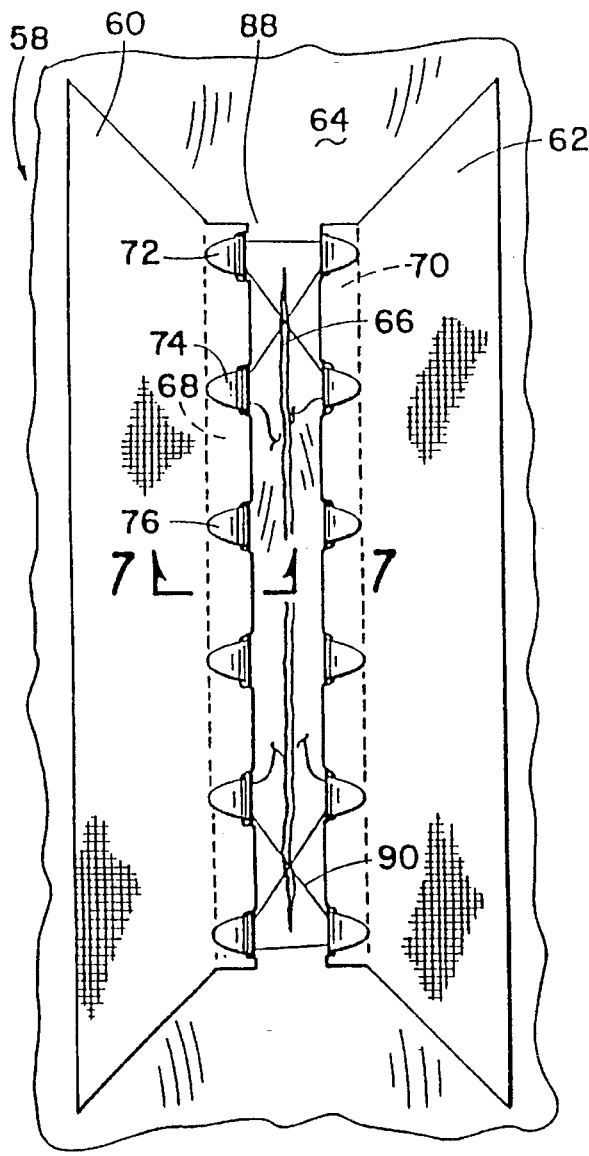
Fig. 6
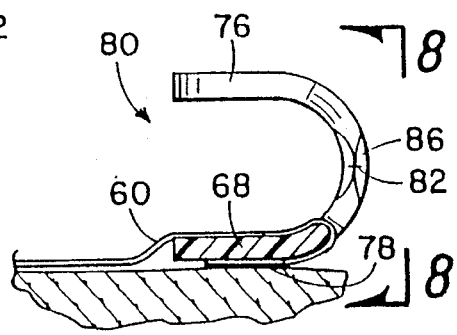
Fig. 7
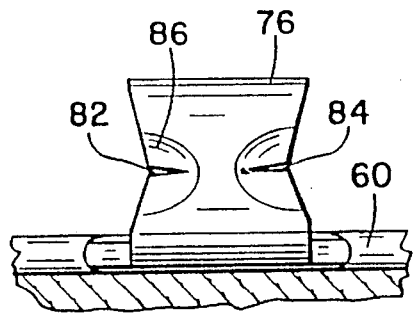
Fig. 8
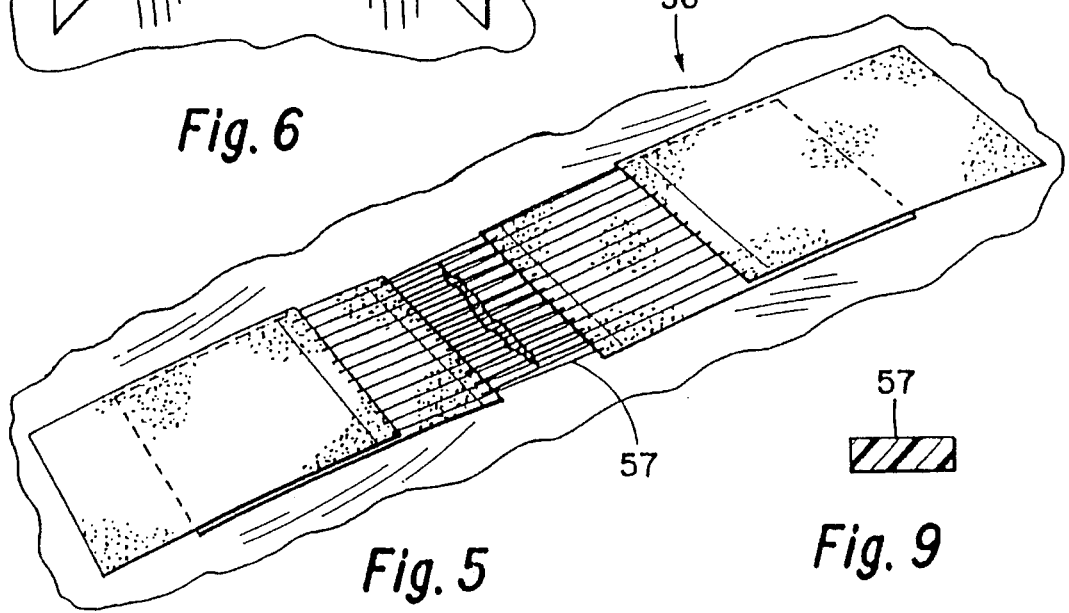
Fig. 5
Fig. 9

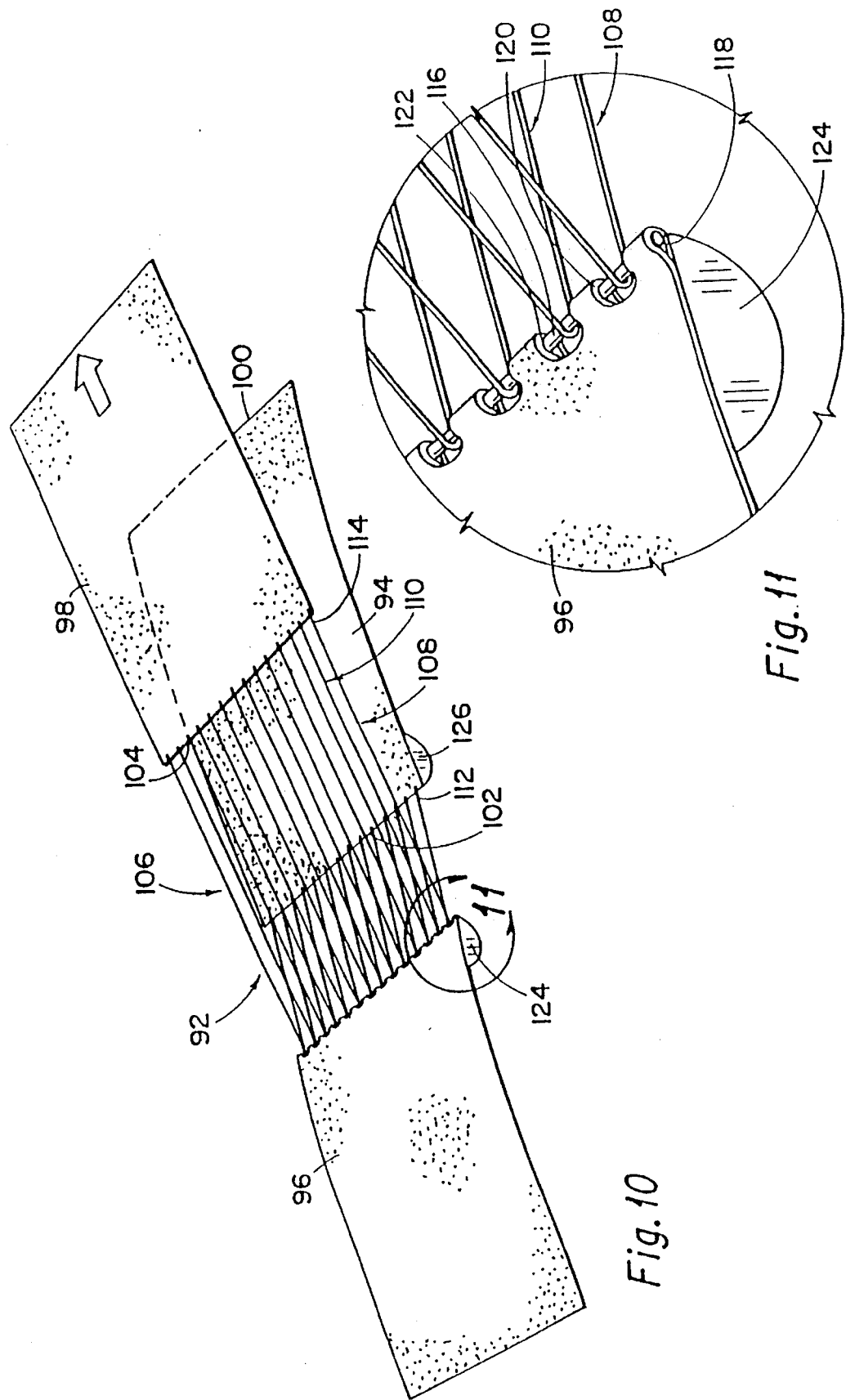

5,534,010

CLOSURE FOR A SKIN WOUND OR INCISION

BACKGROUND OF THE INVENTION

1. Field of the Invention

The present invention relates to a sutureless closure for a skin wound or incision and more particularly to such a closure in which a plurality of parallel filaments disposed between opposing ends of tape strips compress and draw together the incision or wound.

2. Description of the Related Art

There are numerous prior art devices and methods for closing surgical incisions or wounds. The terms incision and wound are referred to herein interchangeably as the present invention may be utilized to close both surgical incisions and wounds.

In the prior art, adhesive bandages may be used to cover a wound as well as draw the edges thereof together to facilitate healing. Wounds and surgical incisions are sometimes sutured together using filament and a needle. U.S. Pat. No. 4,825,866 to Pierce discloses a wound closure device in which VELCRO attaching means are adhered to either side of a wound for drawing together and securing the opposite sides of the wound. The Pierce device does not provide any pressure against the wound which is a recognized technique for promoting healing.

U.S. Pat. No. 4,423,731 to Roomi discloses a surgical dressing in which two strips of adhesive plaster lie along either side and parallel to a wound. Each strip has filaments secured at spaced intervals along one side thereof. The free ends of the filaments are secured to two additional plaster strips which adhere to the skin at a region further away from the wound.

The Roomi device suffers from a number of disadvantages. First, the filaments in Roomi are applied to skin both across the incision and between the plaster strips on each side of the incision. The threads tend to initate the skin when pressed thereagainst. Also, the threads in Roomi are very widely spaced, apparently somewhere in the range of two to three threads per inch. The wound or incision could be better drawn together with more threads per inch. In addition, a sufficient number of threads would apply pressure against the wound similar to a gauze pad which promotes healing.

The filaments in the Roomi dressing are connected to the sides of elongate plaster strips. More tension could be applied if the threads were connected to the end of the strips. In addition, connecting filaments to the end of the strips produces a much narrower bandage which would permit using more bandages per wound. This would enable connecting each closure with different levels of tension. This may be desirable in the case where the wound or incision depth varies or where vascular concentrations might require more tension in the filaments for optimum healing.

SUMMARY OF THE INVENTION

In one aspect, a sutureless closure for a generally elongate wound or incision comprises first and second strips of adhesive tape each being adapted to adhere to a person's skin adjacent the lengthwise extending edges of the wound. The longitudinal axes of the tapes are oriented substantially normal to the wound. A third strip of adhesive tape has a plurality of filaments secured at spaced intervals along one end and coupled to an end of the first tape. A fourth strip of adhesive tape has a plurality of filaments secured at spaced intervals along one end and coupled to an end of the second tape. The third and fourth tapes each adhere to the exposed surface of the first and second tapes with the longitudinal axes thereof substantially normal to the wound so that the filament tension between the tapes draw the edges of the wound together. In another aspect, the sutureless closure comprises first and second strips of adhesive tape each being adapted to adhere to a persons skin adjacent the lengthwise extending edges of the wound. The longitudinal axis of the tapes are substantially parallel to the wound. A plurality of hooks are mounted along the length of each tape. Each hook includes an opening facing away from the wound when the closure is in use. The opening is adapted to receive a filament disposed around the opposing hooks for drawing the edges of the wound together responsive to tension in the filament. A method for closing a generally elongate wound or incision is also provided.

It is a general object of the present invention to provide a sutureless closure for a skin wound or incision which overcomes the above-enumerated disadvantages associated with prior an closures.

It is another object of the present invention to provide such a closure which facilitates application to irregular wounds in tissues by applying several devices, each of which may be differently tensioned, thereto.

It is another object of the present invention to provide such a closure which minimizes exposure of skin to the tensioned filaments.

It is still another object of the present invention to provide such a closure in which the wound is drawn together and compressed to promote healing thereof.

It is yet another object of the present invention to provide such a closure in which greater tension than in prior art devices may be applied to the filaments.

The foregoing and other objects, features and advantages of the invention will become more readily apparent from the following detailed description of a preferred embodiment which proceeds with reference to the drawings.

BRIEF DESCRIPTION OF THE DRAWINGS

FIGS. 1–4 are perspective views of a device constructed in accordance with the present invention in progressive stages of application to a wound or incision.

FIG. 5 is a perspective view of a second device constructed in accordance with the present invention applied to a wound or incision.

FIG. 6 is a plan view of a second embodiment applied to a wound or incision.

FIG. 7 is an enlarged view taken along lines 7—7 in FIG. 6.

FIG. 8 is a view taken along lines 8—8 in FIG. 7.

FIG. 9 is an enlarged cross-sectional view of one of the filaments in FIG. 5.

FIG. 10 is a perspective view of another device constructed in accordance with the present invention.

FIG. 11 is an enlarged view of a portion of the view of FIG. 10.

DETAILED DESCRIPTION OF THE PREFERRED EMBODIMENT

Indicated generally at 10 in FIGS. 1–4 is a sutureless closure constructed in accordance with the present invention. Closure 10 is illustrated in FIG. 1 prior to performance of any of the steps necessary to apply the closure to a wound. Closure 10 is shown in FIG. 4 applied to a wound. Intermediate FIGS. 2–4 illustrate the closure in progressive stages of preparation for applying it to a wound which is described hereinafter.

Closure 10 includes first, second, third and fourth strips of adhesive tape 12, 14, 16, 18, respectively, each of which is about one inch wide, although embodiments ranging in width from much smaller, e.g., 1/16", to much larger, e.g., 4", are contemplated as being within the scope of the invention. Each tape strip includes an exposed nonadhesive upper surface 20, 22, 24, 26. Each tape strip further includes a lower surface, not visible in the drawings, which is coated with adhesive. The tape may be elastic. In FIG. 1, the lower surfaces of tape strips 12, 18, is covered by a fast protective paper strip 28 while the lower surfaces of tape strips 14, 16 is covered by a second protective paper strip 30.

Paper strip 28 is generally equal to the width of tape strips 12, 18 and includes a surface 32 which is on the other side of the surface stuck to the adhesive on tapes 12, 18. Strip 28 is generally rectangular and includes a pair of opposed ends 31, 33. Three transverse creases 36, 38, 40 are formed in the paper strip. Creases 36, 40 are folded in the same direction with crease 38 being folded in the opposite direction to provide an accordion-type fold in strip 28. That portion of strip 28 between crease 40 and end 33 comprises a tab 42.

Protective paper strip 30 is substantially identical to strip 28 and also includes a tab 44. Neither of tabs 42, 44 is stuck to the adhesive on the tape strips.

A plurality of filaments indicated generally at 46 are connnected between an end of tape strip 18 and an end of tape strip 14. The filaments may be elastic or non-plastic and either round or flat ribbon-like strands of monofilament, multifilament or woven materials and may be coated with a nonsticking substance known in the art. The filaments may be molded integral with or attached to their associated tape strips by a sewing or weaving technique, gluing or by bonding. In the present embodiment of the invention, filaments 46 are in substantially parallel relation and are spaced approximately 13 filaments per inch in the present embodiment.

Indicated generally at 48 are filaments which are connected between the ends of strips 16, 12. Like filaments 46, filaments 48 are in parallel relation and are alternately interwoven with filaments 46. The interwoven filaments thus have a density of approximately 26 filaments per inch in the present embodiment.

Polyamide members 50, 52 are mounted on opposing ends of tape strips 12, 14. The polyamide members are semi-circular in cross section with a flat elongate side of each member being stuck to the adhesive on the lower side of each tape adjacent the tape end. Each of members 50, 52 is formed from an elastomeric polyamide.

Considering now the operation of closure 10, initially one of tabs 42, 44 is pulled to expose the adhesive on the lower surface of tape 12, for tab 42, or tape 14, for tab 44. The exposed adhesive is pressed against skin adjacent a wound or incision 54, as illustrated in FIG. 4.

Next, the other tab is pulled to expose the adhesive on the lower side of the other of tapes 12, 14 so that closure 10 is configured as illustrated in FIG. 2. The other exposed adhesive is taped to the skin adjacent wound 54 as illustrated in FIG. 4 so that members 50, 52 are substantially parallel with each other, and with wound 54. Each member is spaced away from the wound substantially the same distance.

Next, one of protective paper strips 28, 30 is pulled until the strip is entirely removed from the adhesive on the tape. By way of illustration in FIGS. 3 and 4, strip 30 is pulled off until tape strip 16 is exposed whereupon strip 16 is taped onto the exposed surface of tape 14 and partially onto exposed skin beyond the end of strip 14. As strip 16 is pressed onto the skin, it is also pulled away from strip 12 in the direction of the filaments so as to tension the filaments and cause member 52 to mound up flesh between wound 54 and member 52 as illustrated in FIG. 4. Member 52 frictionally engages the skin surface and thus causes the flesh mounding when tension is applied to filaments 48. Similarly, when tape 18 is stuck onto tape 12, and to the skin beyond tape 12, tension is applied to the tape to cause member 52 to be pulled toward wound 54 and thus mound flesh between members 50, 52 as illustrated. The flesh is thus pushed up so that the wound receives a very slight pressure from the filaments passing thereover. Both the mounding of flesh and pressure against the wound is known in the art to promote healing.

Turning now to FIG. 5 indicated generally at 56 is a second embodiment of a sutureless closure constructed in accordance with the present invention. Closure 56 is substantially identical to closure 10 except that there are no polyamide members, like members 50, 52 in FIG. 1. Thus, the filaments, one of which is filament 57, disposed over the wound bear directly against it. While there may be some mounding effect by virtue of tension in the filaments which is maintained by the tapes sticking to the skin on opposite sides of the wound, it is not as pronounced as in closure 10. Closure 56 does, however, compress the wound and tend to pull the opposing edges together to promote healing.

It should be noted that both closures 10, 56 facilitate use of multiple closures on a single wound or incision. When so applied, the tension in the filaments from one closure to another may vary as a result of varying tension in each closure when the adhesive is pressed down.

In the present embodiment of the invention, the filaments, like filament 57 in FIG. 5, comprise a ribbon, as best viewed in cross-section in enlarged FIG. 9, having substantially flat upper and lower surfaces with the lower surface beating against the skin. It should be noted that a similar ribbon-shaped filament may be equally well used in closure 10, in FIGS. 1–4. The flat surface of the filament bearing against the skin reduces irritation relative to a round filament.

Turning now to FIGS. 6–8, indicated generally at 58 in FIG. 6 is a third embodiment of a sutureless closure constructed in accordance with the present invention. Closure 58 includes a first and second strip of adhesive tape 60, 62. In the view of FIG. 6, tapes 60, 62 are shown taped onto a skin surface 64 having an incision or wound 66 therein.

A pair of substantially identical rigid polyamide members 68, 70 extend along the length of each of tapes 60, 62, respectively. A plurality of hooks, like hooks 72, 74, 76 are formed integrally with member 68. Member 68 is secured to tape 60 adjacent an edge thereof. The adhesive on the underside of tape 60 sticks to the upper surface of member 68 as viewed in FIG. 7 thereby securing it to the tape. At each hook, a notch is cut in the tape to permit a portion 78 of the tape to be folded over one edge of member 68 and adhered to the lower surface thereof.

Each hook has an opening, like the opening indicated generally at 80 for hook 76. A pair of opposed notches 82, 84 are formed in hook 76. Notch 82 is formed in a portion 86 of the hook having a reduced thickness. In the present embodiment of the invention, the reduced thickness of portion 86 is equal to approximately 0.01 inch adjacent the edges of notch 82. Notch 84 is similarly formed in an opposing portion of the hook. Each of the other hooks on member 68 is substantially identical to hook 76. Member 70 and its corresponding hooks are substantially identical to member 68 and the hooks associated therewith.

A surgical filament 88 is threaded into the openings of hook 72 and the hook opposite therefrom. Another filament 90 is similarly threaded into openings of hooks on the other end of closure 58.

Consideration will now be given to the manner in which closure 58 is applied. First, protective paper strips (not shown) which are stuck against the adhesive on the lower surface of tape 60, 62 are removed and each of tapes 60, 62 is taped onto skin surface 64 adjacent wound 66 as shown in FIG. 6.

Next, filament 88 is wound around the hooks as shown in FIG. 6. At each hook, the filament is pulled into a notch, like notches 82, 84 in hook 76, to secure it at the hook. Prior to securing the filament in a notch on a hook on the other side of the wound, tension in the filament is adjusted. When tension is at the desired level, the filament is then secured by winding it around the hook at the opening and into one of the notches. The filament is then placed into the opposing notch on the same hook and extended across the wound to another hook on the opposite side where the procedure is repeated. It can thus be seen that selected different levels of tension may be placed on each filament run between opposed hooks. This facilitates applying the desired level of tension dependent upon the depth of the wound or vascular concentration.

It may also be desireable to utilize different filaments, like filament 90, rather than one continuous filament as in lacing a boot. Optimum wound closure may be obtained by lacing a filament in the approximate middle of the wound mid-way between the ends of closure 58 and thereafter lacing one end with a second filament, like filament 88, and the other end with a third filament, like filament 90. The filament may be secured to the last hook to which it is connected by wrapping the filament multiple times around the opposing notches, like notch 82, 84, to secure it firmly to the hook.

Turning now to FIGS. 10 and 11, indicated generally at 92 is another embodiment of a sutureless closure constructed in accordance with the present invention. Included therein is a first tape strip 94, a second tape strip 96 and a third tape strip 98. Like previously described tape strips herein, each of the strips includes an adhesive underside. Tape strips 94, 96 are adapted to be secured on opposite sides of a wound or incision and tape 98 is adapted to be secured in part to the upper surface of tape strip 94 and in part to skin extending beyond a distal end 100 of strip 94. Strips 94, 98 each include ends 102, 104 to which a plurality of filaments, indicated generally at 106, are secured. The filaments are secured in the same manner as described in connection with the previous embodiments.

Each of the filaments, like filaments 108, 110 include a first end, like end 112 on filament 108, and a second end, like end 114 on filament 108, which are secured to tape strips 94, 98, respectively.

Each filament also includes a central portion, some of which are viewable in FIG. 11, which is received over an elongate relatively stiff cylindrical member 116. In the present embodiment of the invention, member 116 comprises a monofilament line several times the diameter of each of filaments 106 and extending transversely across tape 96. An end 118 of the tape is folded upon itself so that adhesive portions of tape 96 are stuck to one another. Openings, like openings 120, 122 are cut into the end of the tape to permit each filament, like filaments 110, 108, to be slidably received over member 116.

Polyamide members 124, 126 serve the same function as described in connection with the embodiment of FIG. 1 or can be eliminated as in FIG. 5.

An elongate protective paper strip (not shown) having a transverse crease can be applied to tapes 98, 100 in the same fashion as such strips are applied to opposing sides of the embodiment of FIG. 1. Similarly, a strip can be applied to the adhesive surface of tape 96 thereby preventing the same from sticking before use.

In operation, the paper strips are removed as previously described, strips 94, 96 are secured to opposing sides of an elongate wound and force is applied to strip 98 in the direction of the arrow thereon. As force is applied, filaments 106 come under tension thereby causing the filaments to draw the wound together as previously described. When an appropriate level of tension is placed on the filaments, tape 98 is secured, using the adhesive on the underside thereof, to the upper surface of tape 94 and/or to skin adjacent tape 94. This structure allows for a speedy application and, with practice, application using only one hand.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

I claim:

1. A sutureless closure for a generally elongate wound or incision comprising:

a first strip of tap having an exposed upper nonadhesive surface and having a lower surface coated with adhesive adapted to adhere to skin adjacent the lengthwise extending edges of the wound;

a second strip of adhesive tape adapted to adhere to skin adjacent the lengthwise extending edges of the wound on the opposite side of said wound from said first strip;

a third strip of adhesive tape adapted to adhere to the exposed surface of said first adhesive tape;

a plurality of filaments having a first end coupled to an end of said first tape and a second end coupled to an end of said third tape, said filaments being slidingly received over structure defined on said second strip; and means for frictionally engaging the skin closely adjacent the opposing ends of said first and second tapes when said closure is in use whereby tension in the filaments draws tissue between said engaging means into a slight mound, said engaging means comprising an elongate polyamide member mounted on each of said tapes normal to the longitudinal axis thereof.

2. The sutureless closure of claim 1 wherein said engaging means has a semicircular cross section with a rounded portion directed toward the skin when said closure is in use and a flat portion adhered to the adhesive tape of said first and second strips.

3. The sutureless closure of claim 1 wherein the structure defined on said second strip comprises means for slidably receiving a central portion of each of said filaments.

4. A sutureless closure for a generally elongate wound or incision comprising:

a first strip of tape having an exposed upper nonadhesive surface and having a lower surface coated with adhesive adapted to adhere to skin adjacent the lengthwise extending edges of the wound;

a second strip of adhesive tape adapted to adhere to skin adjacent the lengthwise extending edges of the wound on the opposite side of said wound from said first strip;

a third strip of adhesive tape adapted to adhere to the exposed surface of said first adhesive tape;

a plurality of filaments having a first end coupled to an end of said first tape and a second end coupled to an end of said third tape, said filaments being slidingly received over structure defined on said second strip; and an elongate protective strip for covering the adhesive on said first and third tapes, said strip preventing said adhesive from sticking prior to use of said closure, said protective strip including a pair of transverse creases to permit each of the adhesive tapes which the protective strip covers to be covered by the same side of said strip.

5. The sutureless closure of claim 4 wherein the structure defined on said second strip comprises means for slidably receiving a central portion of each of said filaments.

6. A sutureless closure for a generally elongate wound or incision comprising:

a first strip of tape having an exposed upper nonadhesive surface and having a lower surface coated with adhesive adapted to adhere to skin adjacent the lengthwise extending edges of the wound;

a second strip of adhesive tape adapted to adhere to skin adjacent the lengthwise extending edges of the wound on the opposite side of said wound from said first strip;

a third strip of adhesive tape adapted to adhere to the exposed surface of said first adhesive tape;

a plurality of filaments having a first end coupled to an end of said first tape and a second end coupled to an end of said third tape, said filaments being slidingly received over structure defined on said second strip, with the longitudinal axes of said strips oriented substantially normal to the wound; and an elongate protective strip for covering the adhesive on said first and third tapes, said strip preventing said adhesive from sticking prior to use of said closure, said protective strip including a pair of transverse creases to permit each of the adhesive tapes which the protective strip covers to be covered by the same side of said strip.

7. The sutureless closure of claim 6 which further includes means for frictionally engaging the skin closely adjacent the opposing ends of said first and second tapes when said closure is in use whereby tension in the filaments draws tissue between said engaging means into a slight mound, said engaging means comprising an elongate polyamide member mounted on each of said tapes normal to the longitudinal axis thereof.

8. The sutureless closure of claim 7 wherein said engaging means has a semicircular cross section with a rounded portion directed toward the skin when said closure is in use and a flat portion adhered to the adhesive tape of said first and second strips.

9. A sutureless closure for a generally elongate wound or incision comprising:

a first strip of tape having an exposed upper nonadhesive surface and having a lower surface coated with adhesive adapted to adhere to skin adjacent the lengthwise extending edges of the wound;

a second strip of adhesive tape adapted to adhere to skin adjacent the lengthwise extending edges of the wound on the opposite side of said wound from said first strip;

a third strip of adhesive tape adapted to adhere to the exposed surface of said first adhesive tape;

a plurality of filaments having a first end coupled to an end of said first tape and a second end coupled to an end of said third tape, said filaments being slidingly received over structure defined on said second strip;

an elongate protective strip for covering the adhesive on said first and third tapes, said strip preventing said adhesive from sticking prior to use of said closure, said protective strip including a pair of transverse creases to permit each of the adhesive tapes which the protective strip covers to be covered by the same side of said strip; and means for frictionally engaging the skin closely adjacent the opposing ends of said first and second tapes when said closure is in use whereby tension in the filaments draws tissue between said engaging means into a slight mound, said engaging means comprising an elongate polyamide member mounted on each of said tapes normal to the longitudinal axis thereof.

10. The sutureless closure of claim 9 wherein said engaging means has a semicircular cross section with a rounded portion directed toward the skin when said closure is in use and a flat portion adhered to the adhesive tape of said first and second strips.

* * * * *

UNITED STATES PATENT AND TRADEMARK OFFICE
CERTIFICATE OF CORRECTION

PATENT NO. : 5,534,010
DATED : July 9, 1996
INVENTOR(S) : Meldon L. Peterson

It is certified that error appears in the above-indentified patent and that said Letters Patent is hereby corrected as shown below:

Column 1, line 37, change "filaments in" to --filaments used in--;

Column 1, line 39, change "initate" to --irritate--;

Column 2, line 21, change "an" to --art--;

Column 3, line 15, change "fast" to --first--;

Column 3, line 32, change "non-plastic" to --non-elastic--;

Column 4, line 39, change "beating" to --bearing--;

Column 5, line 66, change "he" to --be--;

Column 6, line 5, change "he" to --be--;

Signed and Sealed this

Eighth Day of July, 1997

*Attest:*

BRUCE LEHMAN

*Attesting Officer*  Commissioner of Patents and Trademarks